United States Patent
Schmidt et al.

(10) Patent No.: US 7,125,675 B2
(45) Date of Patent: Oct. 24, 2006

(54) METHOD FOR INHIBITING TUMOR INVASION OR SPREADING IN A SUBJECT

(75) Inventors: Ann Marie Schmidt, Franklin Lakes, NJ (US); David Stern, Great Neck, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/851,071

(22) Filed: May 8, 2001

(65) Prior Publication Data

US 2002/0177550 A1 Nov. 28, 2002

Related U.S. Application Data

(62) Division of application No. 09/062,365, filed on Apr. 17, 1998, now Pat. No. 6,465,422.

(51) Int. Cl.
*G01N 33/53* (2006.01)
*C12Q 1/00* (2006.01)
*C12N 5/00* (2006.01)

(52) U.S. Cl. .............................. 435/7.1; 435/4; 435/375

(58) Field of Classification Search .................... 514/2, 514/10, 11; 530/300, 350, 351, 387.1, 387.7; 435/4, 6, 7.1, 174; 425/325, 375
See application file for complete search history.

(56) References Cited

U.S. PATENT DOCUMENTS 5,767,071 A * 6/1998 Palladino et al. .............. 514/11
5,981,478 A * 11/1999 Ruoslahti et al. .............. 514/10

FOREIGN PATENT DOCUMENTS

WO WO9822138 5/1998

OTHER PUBLICATIONS

Chintala et al. Modulation of matrix metalloprotease-2 and invasion in human glioma cells by alpha 3 beta 1 integrin. Cancer Lett. Jun. 5, 1996;103(2):201-8.*
Seftor et al. Role of the alpha v beta 3 integrin in human melanoma cell invasion. Proc Natl Acad Sci U S A. Mar. 1, 1992;89(5):1557-61.*
Gehlsen et al, JCB 106:925-930, 1988.*
Miki et al. Biochem Biophys Res Commun 196(2):984-9, 1993.*
Blau et al. (1995) "Molecular Medicine: Gene Therapy—A Novel Form of Drug Delivery" *N. Engl. J. Med.* 333(18): 1204-1207.
Chen, et al. (1997) "Amyloid-beta Peptide-Receptor for Advanced Glycation Endproduct Interaction Elicits Neuronal Expression of Macrophage-Colony Stimulating Factor" *Proc. Natl. Acad. Sci.* 94(10): 5296-5301.
Hori, O. et al. (1995) "The Receptor for Advanced Gylcation End Products (RAGE) Is a Cellular Binding Site for Amphoterin" *J. Biol. Chem.*, 270(43): 25752-25761.
Hori et al. (1995) "The Receptor for Advanced Glycation Endproducts (RAGE) Is A Cell Surface Receptor for Amphoterin in the Developing Central Nervous System (CNS) to Promote Neurite Outgrowth" *FASEB J.*, 9(3): A382.
Hori et al. (1997) "The Receptor for Advanced Gycation Endproducts: Implication for the Development of Diabetic Vascular Disease" *Fundam. Clin. Cardiol.*, 11: 311-329.
Gomez-Navarro et al. (1999) "Gene Therapy For Cancer" *European Journal of Cancer* 35(6): 867-885.
Kelloff et al. (1999) "Cancer Chemoprevention: Progress and Promise" *European Journal of Cancer* 35(14): 2031-2038.
Mastrangelo et al. (1996) "Gene Therapy For Human Cancer: An Essay For Clinicians" *Seminars in Oncology* 23(1): 4-21.
Mohan, P. S. et al. (1992) "Sulfoglycolipids Bind to Adhesive Protein Amphoterin (P30) in the Nervous System" *Biochem. & Biophys. Research Comm.*, 182(2): 689-696.
Neeper, M. et al. (1992) "Cloning and Expression of a Cell Surface Receptor for Advanced Glycosylation End Products of Proteins" *J. Biol. Chem.*, 267(21): 14998-15004.
Price, J. T. et al. (1997) "The Biochemistry of Cancer Dissemination" *Critical Reviews in Biochemistry and Molecular Biology*, 32(3): 175-253.
Schmidt, A. M. et al. (1992) "Isolation and Characterization of Two Binding Proteins for Advanced Glycolation End Products from Bovine Lung Which Are Present on the Endothelial Cell Surface" *J. Biol. Chem.*, 267 (21): 14987-14997.
Schmidt et al. (1997) "V-domain of Receptor for Advanced Glycation Endproducts (RAGE) Mediates Binding of AGEs: A Novel Target for Therapy of Diabetic Complications" *Circulation*, 96(8): I37.

(Continued)

*Primary Examiner*—Sumesh Kaushal
(74) *Attorney, Agent, or Firm*—John P. White, Esq.; Cooper & Dunham LLP (57) ABSTRACT

The present invention provides for a method for inhibiting tumor invasion or metastasis in a subject which comprises administering to the subject a therapeutically effective amount of a form of soluble Receptor for Advanced Glycation Endproducts (RAGE). The present invention also provides a method for evaluating the ability of an agent to inhibit tumor invasion in a local cellular environment which comprises: (a) admixing with cell culture media an effective amount of the agent; (b) contacting a tumor cell in cell culture with the media from step (a); (c) determining the amount of spreading of the tumor cell culture, and (d) comparing the amount of spreading of the tumor cell culture determined in step (c) with the amount determined in the absence of the agent, thus evaluating the ability of the agent to inhibit tumor invasion in the local cellular environment. The present invention also provides a pharmaceutical composition which comprises a therapeutically effective amount of the agent evaluated in the aforementioned method and a pharmaceutically acceptable carrier.

7 Claims, 6 Drawing Sheets

OTHER PUBLICATIONS

Schmidt, A. M. et al. (1998) "RAGE: A Receptor with a Taste for Multiple Ligands and Varied Pathophysiologic States" *Hormones and Signaling*, 1: 41-63.

Schmidt et al. (1999) "Activation of Receptor for Advanced Glycation End Products A Mechanism for Chronic Vascular Dysfunction in Diabetic Vasculopathy and Atherosclerosis" *Circ. Res.* 84: 489-497.

Sigh, S. P. et al (1997) "Role of Gqa in Insulin-Stimulated Glucose Uptake by C6 Glioma Cells" *NeuroReport*, 8:2359-2263.

Taguchi et al. (2000) "Blockade of RAGE-amphoterin Signalling Suppresses Tumour Growth and Metastases" *Nature* 405: 354-360.

Yan, S. D. et al. (1997) "Amyloid-β Peptide-Receptor for Advanced Glycation Endproduct Interaction Elicits Neuronal Expression of Macrophage-colony stimulating Factor: A Proinflammatory Pathway in Alzheimer Disease" *Proc. Natl. Acad. Sci. USA*, 94: 5296-5301 and.

Yan, S. D. et al. (1996) "RAGE and Amyloid-β Peptide Neurotoxicity in Alzheimer's Disease" *Nature*, 382: 685-691.

Taguchi, A., et al. (1998) Soluble Receptor for AGE (sRAGE) Suppresses Growth of C6 Glioma Tumors in Nude Mice. FASEB J., Abstract No. 5502:A950.

Taguchi, A., et al. (1999) Blockage of Amphoterin-Receptor for AGE (RAGE) Interaction Suppresses Lung Metastasis in Murine Lewis Lung Carcinoma. FASEB J., Abstract No. 292.9:A363.

Parkkinen, J., et al. (1993) Amphotherin, the 30-kDa protein in a family of HMG1-type polypeptides. *J. Bio Chem.* 268(26) :19726-38.

Supplementary Partial European Search Report, Oct. 1, 2004 from European Patent Office on European Patent Application No. EP 99916699. 4-2405.

U. S. Appl. No. 09/689,469, filed Oct. 12, 2000, Ann Marie Schmidt and David Stern.

* cited by examiner

SEQUENCE LISTING

<160> NUMBER OF SEQ ID NOS: 6

<210> SEQ ID NO 1
<211> LENGTH: 332
<212> TYPE: PRT
<213> ORGANISM: Human

<400> SEQUENCE: 1

```
Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80
```

-continued

Asn Arg Asn Gly Lys Glu Thr Lys Ser Asn Tyr Arg Val Arg Val Tyr
                85                  90                  95
Gln Ile Pro Gly Lys Pro Glu Ile Val Asp Ser Ala Ser Glu Leu Thr
            100                 105                 110
Ala Gly Val Pro Asn Lys Val Gly Thr Cys Val Ser Glu Gly Ser Tyr
        115                 120                 125
Pro Ala Gly Thr Leu Ser Trp His Leu Asp Gly Lys Pro Leu Val Pro
    130                 135                 140
Asn Glu Lys Gly Val Ser Val Lys Glu Gln Thr Arg Arg His Pro Glu
145                 150                 155                 160
Thr Gly Leu Phe Thr Leu Gln Ser Glu Leu Met Val Thr Pro Ala Arg
                165                 170                 175
Gly Gly Asp Pro Arg Pro Thr Phe Ser Cys Ser Phe Ser Pro Gly Leu
            180                 185                 190
Pro Arg His Arg Ala Leu Arg Thr Ala Pro Ile Gln Pro Arg Val Trp
        195                 200                 205
Glu Pro Val Pro Leu Glu Glu Val Gln Leu Val Val Glu Pro Glu Gly
    210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                245                 250                 255
Pro Leu Pro Pro Ser Pro Val Leu Ile Leu Pro Glu Ile Gly Pro Gln
            260                 265                 270
Asp Gln Gly Thr Tyr Ser Cys Val Ala Thr His Ser Ser His Gly Pro
        275                 280                 285
Gln Glu Ser Arg Ala Val Ser Ile Ser Ile Ile Glu Pro Gly Glu Glu
    290                 295                 300
Gly Pro Thr Ala Gly Ser Val Gly Gly Ser Gly Leu Gly Thr Leu Ala
305                 310                 315                 320
Leu Ala Leu Gly Ile Leu Gly Gly Leu Gly Thr Ala
                325                 330

<210> SEQ ID NO 2
<211> LENGTH: 22
<212> TYPE: PRT
<213> ORGANISM: Human

<400> SEQUENCE: 2

Met Ala Ala Gly Thr Ala Val Gly Ala Trp Val Leu Val Leu Ser Leu
1               5                   10                  15
Trp Gly Ala Val Val Gly
            20

<210> SEQ ID NO 3
<211> LENGTH: 40
<212> TYPE: PRT
<213> ORGANISM: Human

<400> SEQUENCE: 3

Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly Gly Val Val
        35                  40

```
<210> SEQ ID NO 4
<211> LENGTH: 11
<212> TYPE: PRT
<213> ORGANISM: Human

<400> SEQUENCE: 4

Gly Ser Asn Lys Gly Ala Ile Ile Gly Leu Met
1               5                   10

<210> SEQ ID NO 5
<211> LENGTH: 30
<212> TYPE: PRT
<213> ORGANISM: Human

<400> SEQUENCE: 5

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys
            20                  25                  30

<210> SEQ ID NO 6
<211> LENGTH: 10
<212> TYPE: PRT
<213> ORGANISM: Human

<400> SEQUENCE: 6

Ala Gln Asn Ile Thr Ala Arg Ile Gly Glu
1               5                   10
```

METHOD FOR INHIBITING TUMOR INVASION OR SPREADING IN A SUBJECT

This application is a divisional of U.S. Ser. No. 09/062,365, filed Apr. 17, 1998, now U.S. Pat. No. 6,465,422 the contents of which are hereby incorporated by reference into the present application.

The invention disclosed herein was made with Government support under National Institutes of Health Grant No. AG00602 from the Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

An important means by which tumors grow and invade surrounding normal tissue is by a complex series of cell-cell and cell matrix interactions. We have focused on the interaction of tumor cells with matrix-associated components. The Receptor to AGE (RAGE) interacts with a range of physiologically and pathophysiologically-relevant ligands (1–5). In normal developing neurons of the central nervous system, the expression of RAGE is markedly enhanced and co-localizes with that of its ligand, amphoterin. Amphoterin, a matrix-associated polypeptide, is expressed in developing neurons and certain tumor cells, such as rat C6 glioma cells (6–12).

SUMMARY OF THE INVENTION

The present invention provides for a method for inhibiting tumor invasion or metastasis in a subject which comprises administering to the subject a therapeutically effective amount of a form of soluble Receptor for Advanced Glycation Endproducts (RAGE). The present invention also provides a method for evaluating the ability of an agent to inhibit tumor invasion in a local cellular environment which comprises: (a) admixing with cell culture media an effective amount of the agent; (b) contacting a tumor cell in cell culture with the media from step (a); (c) determining the amount of spreading of the tumor cell culture, and (d) comparing the amount of spreading of the tumor cell culture determined in step (c) with the amount determined in the absence of the agent, thus evaluating the ability of the agent to inhibit tumor invasion in the local cellular environment. The present invention also provides a pharmaceutical composition which comprises a therapeutically effective amount of the agent evaluated in the aforementioned method and a pharmaceutically acceptable carrier.

DETAILED DESCRIPTION OF THE INVENTION

The present invention provides for a method for inhibiting tumor invasion or metastasis in a subject which comprises administering to the subject a therapeutically effective amount of a form of soluble Receptor for Advanced Glycation Endproducts (RAGE).

As used herein, a "form of soluble RAGE" encompasses peptides which are derived from naturally occurring RAGE protein. The following are examples of forms of soluble RAGE: mature human soluble RAGE, mature bovine soluble RAGE, mature murine soluble RAGE, fragments or portions of a soluble RAGE. Representative peptides of the present invention include but are not limited to peptides having an amino acid sequence which corresponds to amino acid numbers (2–30), (5–35), (10–40), (15–45), (20–50), (25–55), (30–60), (30–65), (10–60), (8–100), 14–75), (24–80), (33–75), (45–110) of human sRAGE protein. In one embodiment the form of soluble RAGE may consist essentially of any such portion of the human RAGE peptide. In another embodiment, the form of soluble RAGE may consist essentially of a peptide which comprises any such portion of the human RAGE amino acid having the sequence from amino acid at position 1 (alanine) to amino acid number 332 (alanine) (without considering the 22 amino acid leader sequence).

The abbreviations used herein for amino acids are those abbreviations which are conventionally used:

A=Ala=Alanine; R=Arg=Arginine; N=Asn=Asparagine; D=Asp=Aspartic acid; C=Cys=Cysteine; Q=Gln=Glutamine; E=Glu=Gutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

In one embodiment the form of soluble RAGE comprises a peptide having the sequence from alanine at position 1 to alanine at position 332 of human RAGE.

In another embodiment the form of soluble RAGE comprises a peptide of 10–40 amino acids having a sequence taken from within the sequence from alanine at position 1 to alanine at position 332 of human RAGE.

In another embodiment, the form of soluble RAGE comprises a peptide having the following sequence of mature human RAGE.

The following is the amino acid sequence of mature human RAGE (which does not include a 22 amino acid leader sequence):

```
Ala Gln Asn Ile Thr Ala Arg Ile Gly Glu Pro Leu Val Leu Lys

Cys Lys Gly Ala Pro Lys Lys Pro Pro Gln Arg Leu Glu Trp Lys

Leu Asn Thr Gly Arg Thr Glu Ala Trp Lys Val Leu Ser Pro Gln

Gly Gly Gly Pro Trp Asp Ser Val Ala Arg Val Leu Pro Asn Gly

Ser Leu Phe Leu Pro Ala Val Gly Ile Gln Asp Glu Gly Ile Phe

Arg Cys Gln Ala Met Asn Arg Asn Gly Lys Glu Thr Lys Ser Asn

Tyr Arg Val Arg Val Tyr Gln Ile Pro Gly Lys Pro Glu Ile Val

Asp Ser Ala Ser Glu Leu Thr Ala Gly Val Pro Asn Lys Val Gly

Thr Cys Val Ser Glu Gly Ser Tyr Pro Ala Gly Thr Leu Ser Trp

His Leu Asp Gly Lys Pro Leu Val Pro Asn Glu Lys Gly Val Ser

Val Lys Glu Gln Thr Arg Arg His Pro Glu Thr Gly Leu Phe Thr

Leu Gln Ser Glu Leu Met Val Thr Pro Ala Arg Gly Gly Asp Pro

Arg Pro Thr Phe Ser Cys Ser Phe Ser Pro Gly Leu Pro Arg His

Arg Ala Leu Arg Thr Ala Pro Ile Gln Pro Arg Val Trp Glu Pro

Val Pro Leu Glu Glu Val Gln Leu Val Val Glu Pro Glu Gly Gly

Ala Val Ala Pro Gly Gly Thr Val Thr Leu Thr Cys Glu Val Pro

Ala Gln Pro Ser Pro Gln Ile His Trp Met Lys Asp Gly Val Pro

Leu Pro Leu Pro Pro Ser Pro Val Leu Ile Leu Pro Glu Ile Gly

Pro Gln Asp Gln Gly Thr Tyr Ser Cys Val Ala Thr His Ser Ser

His Gly Pro Gln Glu Ser Arg Ala Val Ser Ile Ser Ile Ile Glu

Pro Gly Glu Glu Gly Pro Thr Ala Gly Ser Val Gly Gly Ser Gly

Leu Gly Thr Leu Ala Leu Ala Leu Gly Ile Leu Gly Gly Leu Gly

Thr Ala (Seq I.D. No. --).
```

In one embodiment the form of soluble RAGE comprises a V domain of naturally occuring soluble RAGE. In another embodiment the form of soluble RAGE comprises a C domain of naturally occurring soluble RAGE. The 22 amino acid leader sequence of immature human RAGE is Met Ala Ala Gly Thr Ala Val Gly Ala Trp Val Leu Val Leu Ser Leu Trp Gly Ala Val Val Gly (SEQ ID NO: 2).

In one embodiment the form of soluble RAGE is a peptide expressed by a replicable vector containing nucleic acid encoding the form of soluble RAGE. In one embodiment the form of soluble RAGE is a peptide which corresponds to all or part of soluble RAGE expressed by a replicable vector containing nucleic acid encoding the form of soluble RAGE. In another embodiment the replicable vector is capable of expressing the peptide within a tumor cell in a subject.

In another embodiment the tumor cell is a eukaryotic cell.

In another embodiment the replicable vector is a plasmid, an attenuated virus, a phage, a phagemid or a linear nucleic acid.

In another embodiment, the method further comprises administering a pharmaceutically acceptable carrier to the subject during the administration of the form of soluble RAGE.

In one embodiment the administration is via intralesional, intraperitoneal, intramuscular or intravenous injection; infusion; intrathecal administration; subcutaneous administration; liposome-mediated delivery; or topical, nasal, oral, ocular or otic delivery. As used herein, intrathecal administration includes administration in the cerebrospinal fluid by lumbar puncture.

In one embodiment of the present invention, the subject is a mammal. In another embodiment, the mammal is a human.

In one embodiment, the form of soluble RAGE is administered daily, weekly or monthly. The form of soluble RAGE may be delivered hourly, daily, weekly, monthly, yearly (e.g. in a time release form) or as a one time delivery. The delivery may be continuous delivery for a period of time, e.g. intravenous delivery. The agent or pharmaceutical composition of the present invention may be delivered intercranially or into the spinal fluid. In another embodiment, the therapeutically effective amount comprises a dose from about 0.000001 mg/kg body weight to about 100 mg/kg body weight. In a preferred embodiment, the therapeutically effective amount comprises a dose of from about 100 ng/day/kg body weight to about 200 mg/day/kg body weight.

The present invention also provides a method for evaluating the ability of an agent to inhibit tumor invasion in a local cellular environment which comprises: (a) admixing with cell culture media an effective amount of the agent; (b) contacting a tumor cell in cell culture with the media from step (a); (c) determining the amount of spreading of the tumor cell culture, and (d) comparing the amount of spreading of the tumor cell culture determined in step (c) with the amount determined in the absence of the agent, thus evaluating the ability of the agent to inhibit tumor invasion in the local cellular environment.

In one embodiment the tumor cell is a eukaryotic cell. In another embodiment the tumor cell is a cell of a subject. In a further embodiment, the subject is a human, a mouse, a rat, a dog or a non-human primate.

In a further embodiment, the agent comprises a peptide, a peptidomimetic, a nucleic acid, a synthetic organic molecule, an inorganic molecule, a carbohydrate, a lipid, an antibody or fragment thereof, or a small molecule. The antibody may be a monoclonal antibody. The antibody may be a polyclonal antibody. In one embodiment, the fragment of the antibody comprises a Fab fragment. In another embodiment the fragment of the antibody comprises a complementarity determining region or a variable region.

The agent may be conjugated to a carrier. The peptide or agent may be linked to an antibody, such as a Fab or a Fc fragment for specifically targeted delivery.

In one embodiment the peptide is a synthetic peptide or a peptide analog. The peptide may be a non-natural peptide which has chirality not found in nature, i.e. D-amino acids or L-amino acids. In another embodiment the peptide comprises at least a portion of the sequence -Asp-Ala-Glu-Phe-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val- (Seq. I.D. No. --).

In a further embodiment the peptide comprises at least a portion of the sequence -Gly-Ser-Asn-Lys-Gly-Ala-Ile-Ile-Gly-Leu-Met- (SEQ ID NO: 4). In another embodiment the peptide has the amino acid sequence A-Q-N-I-T-A-R-I-G-E-P-L-V-L-K-C-K-G-A-P-K-K-P-P-Q-R-L-E-W-K (SEQ ID NO: 5).

In another embodiment the peptide has the amino acid sequence A-Q-N-I-T-A-R-I-G-E (SEQ ID No: 6).

In addition to naturally-occurring forms of soluble RAGE, the present invention also embraces other peptides such as peptide analogs of sRAGE. Such analogs include fragments of sRAGE. Following the procedures of the published application by Alton et al. (WO 83/04053), one can readily design and manufacture genes coding for microbial expression of peptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of sRAGE polypeptide. Such products share at least one of the biological properties of sRAGE but may differ in others. As examples, products of the invention include those which are foreshortened by e.g., deletions; or those which are more stable to hydrolysis (and, therefore, may have more pronounced or longerlasting effects than naturally-occurring); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within sRAGE, which fragments may possess one property of sRAGE and not others. It is noteworthy that activity is not necessary for any one or more of the polypeptides of the invention to have therapeutic utility or utility in other contexts, such as in assays of sRAGE antagonism. Competitive antagonists may be quite useful in, for example, cases of overproduction of sRAGE.

The agent of the present invention may be a peptidomimetic which may be at least partially unnatural. The agent may be a small molecule mimic of a portion of the amino acid sequence of sRAGE. The agent may have increased stability, efficacy, potency and bioavailability by virtue of the mimic. Further, the agent may have decreased toxicity. The peptidomimetic agent may have enhanced mucosal intestinal permeability. The agent may be synthetically prepared. The agent of the present invention may include L-, D-, DL- or unnatural amino acids, alpha, alpha-disubstituted amino acids, N-alkyl amino acids, lactic acid (an isoelectronic analog of alanine). The peptide backbone of the agent may have at least one bond replaced with PSI-[CH=CH] (Kempf et al. 1991). The agent may further include trifluorotyrosine, p-Cl-phenylalanine, p-Br-phenylalanine, poly-L-propargylglycine, poly-D,L-allyl glycine, or poly-L-allyl glycine. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

In one embodiment of the present invention the agent is a form of soluble human RAGE. In another embodiment the agent is an extracellular portion human RAGE. In another embodiment the agent inhibits an interaction between the tumor cell and an extracellular matrix molecule. In one embodiment the extracellular matrix molecule is a laminin, a fibronectin, amphoterin, a cadherin, an integrin or a hyaluronic acid. In another embodiment the integrin is an αVβV integrin, an αVβIII integrin, or an αIβII integrin. In another embodiment, the laminin is β1 laminin. In another embodiment the agent inhibits binding of RAGE to amphoterin.

The present invention also provides a pharmaceutical composition which comprises a therapeutically effective amount of the agent evaluated in the aforementioned method and a pharmaceutically acceptable carrier. In one embodiment the carrier is a diluent, an aerosol, a topical carrier, an aqueous solution, a replicable nucleic acid vector, a liposome, a magnetic bead, a nonaqueous solution or a solid carrier.

The actual effective amount will be based upon the size of the subject. The biodegradability of the agent, the bioactivity of the agent and the bioavailability of the agent are factors which will alter the effective amount. The agent may be delivered topically in a creme or salve carrier. It may be reapplied as needed based upon the absorbancy of the carrier to the skin or mucosa or wound. If the agent does not degrade quickly, is bioavailable and highly active, a smaller amount will be required to be effective. The effective amount will be known to one of skill in the art; it will also be dependent upon the form of the agent, the size of the agent and the bioactivity of the agent. One of skill in the art could routinely perform empirical activity tests for a agent to determine the bioactivity in bioassays and thus determine the effective amount.

The present invention also provides a method for inhibiting tumor invasion or metastasis in a subject which comprises administering to the subject a therapeutically effective amount of the aforementioned pharmaceutical composition.

One embodiment of the present invention is a composition which comprises a form of soluble RAGE and a pharmaceutically acceptable carrier. In another embodiment the invention provides a composition which comprises the aforementioned agent and a pharmaceutically acceptable carrier.

As used herein, the term "pharmaceutically acceptable carrier" encompasses any of the standard pharmaceutically accepted carriers, such as phosphate buffered saline solution, acetate buffered saline solution (a likely vehicle for parenteral administration), water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

When administered orally or topically, such agents and pharmaceutical compositions would be delivered using different carriers. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The specific carrier would need to be selected based upon the desired method of deliver, e.g., PBS could be used for intravenous or systemic delivery and vegetable fats, creams, salves, ointments or gels may be used for topical delivery.

Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80,Pluronic F68,bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the agent, complexation with metal ions, or incorporation of the agent into or onto particulate preparations of polymeric agents such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the agent or composition. The choice of compositions will depend on the physical and chemical properties of the agent.

The agent of the present invention may be delivered locally via a capsule which allows sustained release of the agent or the peptide over a period of time. Controlled or sustained release compositions include formulation in lipophilic depots (e.g., fatty acids, waxes, oils). Also comprehended by the invention are particulate compositions coated with polymers (e.g., poloxamers or poloxamines) and the agent coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, agents (such as a peptide comprising the V-domain of sRAGE) are often cleared rapidly from the circulation and may therefore elicit relatively short-lived pharmacological activity. Consequently, frequent injections of relatively large doses of bioactive agents may by required to sustain therapeutic efficacy. Agents modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified agents (Abuchowski et al., 1981; Newmark et al., 1982; and Katre et al., 1987). Such modifications may also increase the agent's solubility in aqueous solution, eliminate aggregation, enhance the physical and chemical stability of the agent, and greatly reduce the immunogenicity and reactivity of the agent. As a result, the desired in vivo biological activity may be achieved by the administration of such polymer-agent adducts less frequently or in lower doses than with the unmodified agent.

Attachment of polyethylene glycol (PEG) to agents is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The agent of the present invention may be delivered in a microencapsulation device so as to reduce or prevent an host immune response against the agent or against cells which may produce the compound. The agent of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Inhibition of Tumor Growth and Spread by Soluble Receptor for Age (sRAGE) in C6-glioma Tumors in Nude Mice An important means by which tumors grow and invade surrounding normal tissue is by a complex series of cell—cell and cell matrix interactions. We have focused on the interaction of tumor cells with matrix-associated components. The Receptor to AGE (RAGE) interacts with a range of physiologically and pathophysiologically-relevant ligands (1–5). In normal developing neurons of the central nervous system, the expression of RAGE is markedly enhanced and co-localizes with that of its ligand, amphoterin. Amphoterin, a matrix-associated polypeptide, is expressed in developing neurons and certain tumor cells, such as rat C6 glioma cells (6–12).

In in vitro experiments, the interaction of neuronal RAGE with amphoterin mediates neurite outgrowth: on amphoterin-coated matrices, neurite outgrowth- is inhibited in the presence of either anti-RAGE $(Fab)_2$ or soluble RAGE (sRAGE; the extracellular two thirds of RAGE). In contrast, blocking access to RAGE had no effect on neurite outgrowth on laminin- or poly-lysine-coated matrices. As in the case of amphoterin, the expression of RAGE decreases after birth in developing rats. Notably, however, the expression of amphoterin is also increased in tumor cells. It has been postulated that in that context, amphoterin may effect matrix degradation by activation of plasminogen: events critical in the ability of tumors to locally invade their immediate environment. Indeed, the ability of tumors to modulate local tissue and vasculature is essential for distal invasion and the development of metastases.

In our studies, we tested the hypothesis that blockade of tumor cell RAGE would interfere with the ability of tumors to compromise the integrity of their local environment, at least in part by disruption of the RAGE (cellular)-amphoterin (matrix) interaction. We demonstrate here that when C6 (rat) glioma cells were transfected with constructs designed to overexpress soluble RAGE (sRAGE) in the local tumor environment, tumor growth was significantly diminished in nude mice. In contrast, mock transfection of C6 glioma cells (vector only) had no effect on tumor growth compared with untreated cells. Similarly, when C6 glioma cells were injected into nude mice, intraperitoneal administration of sRAGE resulted in dose-dependent diminution of tumor size. In contrast, treatment with mouse serum albumin was without effect.

Taken together, our studies indicate that administration of sRAGE may be an important means by which to limit tumor growth in the local environment and, likely, the development of distant metastases. Our studies indicate that interruption of cell (RAGE)-matrix (amphoterin and/or similar structures) is at least one mechanism by which sRAGE limits tumor growth. Our data strongly suggest, however, that sRAGE does not affect the rate of tumor cell growth.

These studies indicate that RAGE may be a novel target for the prevention of local tumor growth and invasion. Soluble RAGE (sRAGE) may thus represent a model structure for the development of agents to limit tumor growth and invasion into the local environment, and, potentially, the development of distant metastases.

Materials and Methods:

Cell culture. C6 glioma cells (rat) we obtained from the American Type Tissue Corporation (ATCC, Rockville, Md.) and characterized as previously described (Singh et al, 1997). Cells were grown as recommended by the ATCC. Transfection of constructs expressing either human soluble RAGE (Neeper et al., 1992) were prepared and transfected into C6 glioma cells using LipoFECTAMINE® (Life Technologies, Grand Island, N.Y.). Stable lines were selected using G418 (Life Technologies). Constructs containing vector alone (mock) were transfected into C6 cells as controls.

Animal studies. NCR nude mice were obtained from Taconic Laboratories. At the age of 8–10 weeks, C6 glioma cells (usually about $10^5$ cells/ml) were injected into the lower backs of the mice. Tumor volume was measured sequentially and recorded. At sacrifice, mice were deeply anesthetized and then tumors removed and weighed.

Preparation of mouse soluble RAGE. Murine soluble RAGE was prepared using a baculovirus-Sf9 cell expression system. Murine sRAGE was purified from cellular supernatant using FPLC Mono S® (Amersham-Pharmacia®) and endotoxin removed using De-Toxigel® columns (Pierce, Rockford, Ill.). The final product was pure based on SDS-PAGE electrophoresis (nonreducing conditions). No detectable endotoxin was found in the final samples (limulus amebocyte assay. Sigma Chemical Co., St. Louis, Mo.). Control mice were treated with mouse serum albumin (MSA: Sigma Chemical Co.)

Injection of sRAGE into mice. Mice were treated immediately upon injection of the tumor cells into the back of the mouse with the indicated dose of sRAGE or mouse serum albumin (equimolar concentration) through the day of sacrifice. Protein was injected intraperitoneally in a volume of 0.1 ml in phosphate-buffered saline.

Quantitation of cell number. C6 glioma cells were grown onto the wells of 96-well plates. On day, cells were fixed and relative cell number determined using the CYQUANT® assay system from Amersham.

Figure 1A:
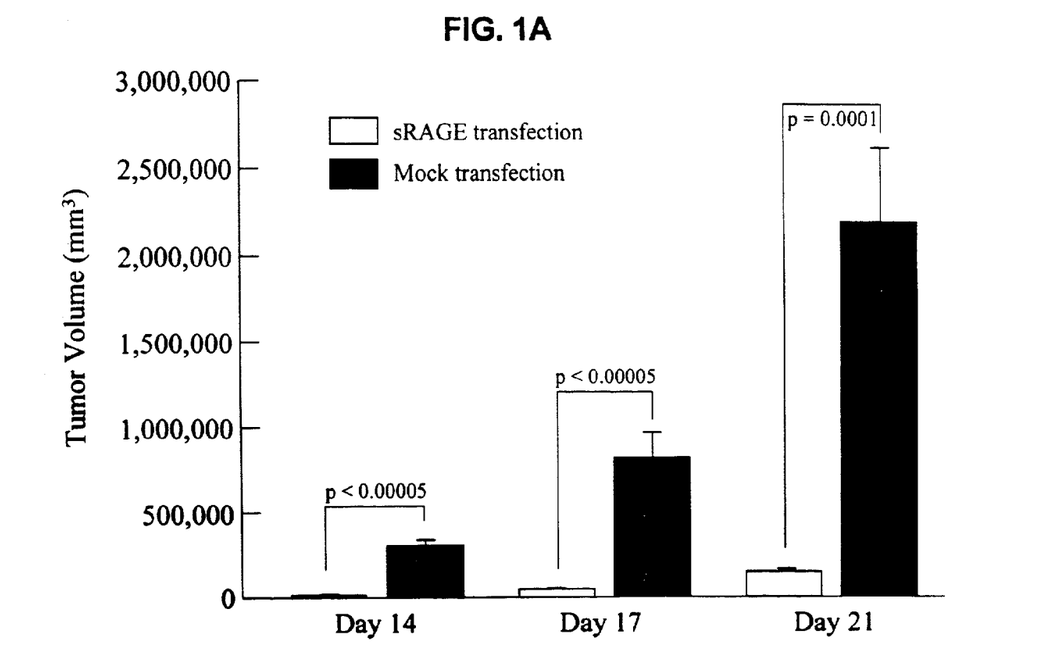
FIGS. 1A–1B. Transfection of C6 glioma cells with constructs expressing sRAGE results in diminished tumor volume compared with mock-transfected tumor cells. $1 \times 10^5$ tumor cells/ml (0.1 ml) were injected into the backs of nude mice. Cells were previously transfected either with constructs overexpressing sRAGE or mock-transfection (vector alone) as described above. At the indicated days after tumor injection, tumor volume was measured. The mean±standard error of the mean is reported. Twenty mice were studied per experimental group. Statistical considerations are indicated. This experiment was repeated three times with analogous results.
Figure 1B:
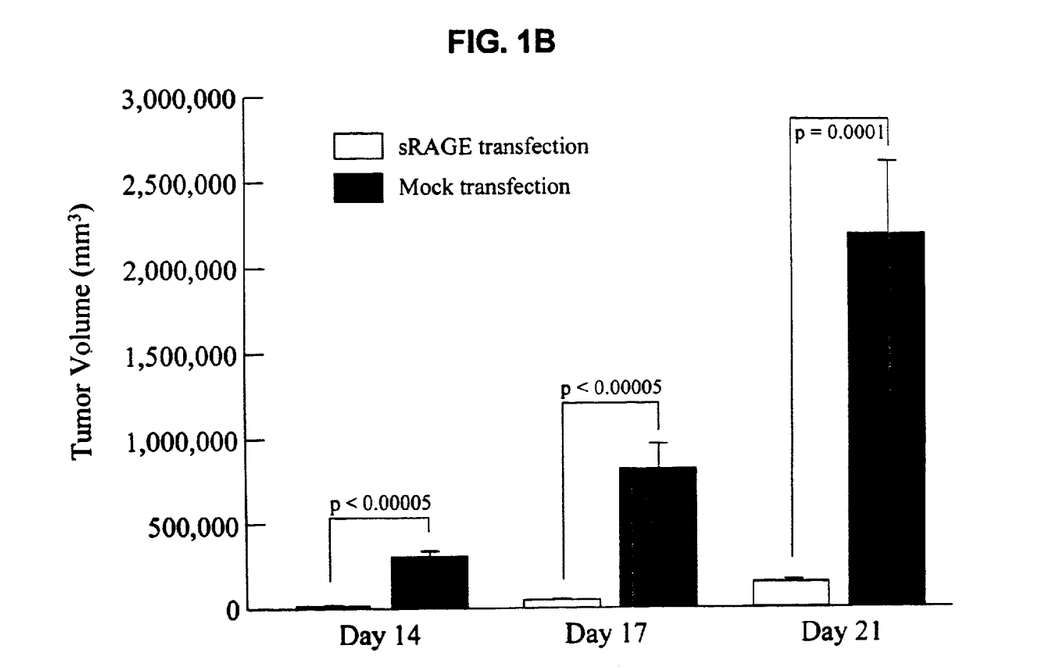

Results:

We first determined by RT-PCR that C6 glioma cells expressed mRNA for RAGE; the presence of RAGE antigen was confirmed by immunohistochemistry. In order to determine if sRAGE might interrupt tumor growth and invasion, we performed two sets of experiments. In the first, C6 glioma cells were transfected with constructs to express either sRAGE or vector alone. In other experiments, C6 glioma cells were injected into nude mice; tumors were generated, and then mice were treated parenterally with either sRAGE or mouse serum albumin.

sRAGE-transfected C6 Glioma Cells.

sRAGE-transfected or mock-transfected C6 glioma cells were injected into nude mice and tumor volume sequentially measured. When tumor volume was measure on days 14, 17 and 21, substantially smaller tumors were observed in sRAGE-transfected cells compared with mock-transfected tumor cells (FIG. 1). On day 14, mean tumor volume in nude mice injected with mock-transfected tumors was $315,276.5 \pm 3,790.4$ $\mu m^3$ vs $27,875.4 \pm 4,199.6$ $\mu m^3$ mean tumor volume in sRAGE-transfected tumor (11.3-fold difference; $p<0.00005$). On day 17, mean tumor volume in nude mice injected with mock-transfected tumor was $823,759 \pm 142,841.5$ $\mu m^3$ vs. $50,645 \pm 5,109.7$ $\mu m^3$ (16.2-fold difference; $p<0.00005$). On day 21, mean tumor volume in nude mice injected with mock-transfected tumor was $2,200,000 \pm 420,235$ $\mu m^3$ vs. $152,000 \pm 22,487.3$ $\mu m^3$ (14.5-fold difference; $p=0.00001$). When evaluated by ELISA, an at least three-fold increase in levels of sRAGE were found in sRAGE-transfected tumors vs. Those transfected with vector alone (mock). Histologic analysis confirmed markedly smaller tumors, with evidence of necrosis.

Figure 2A:
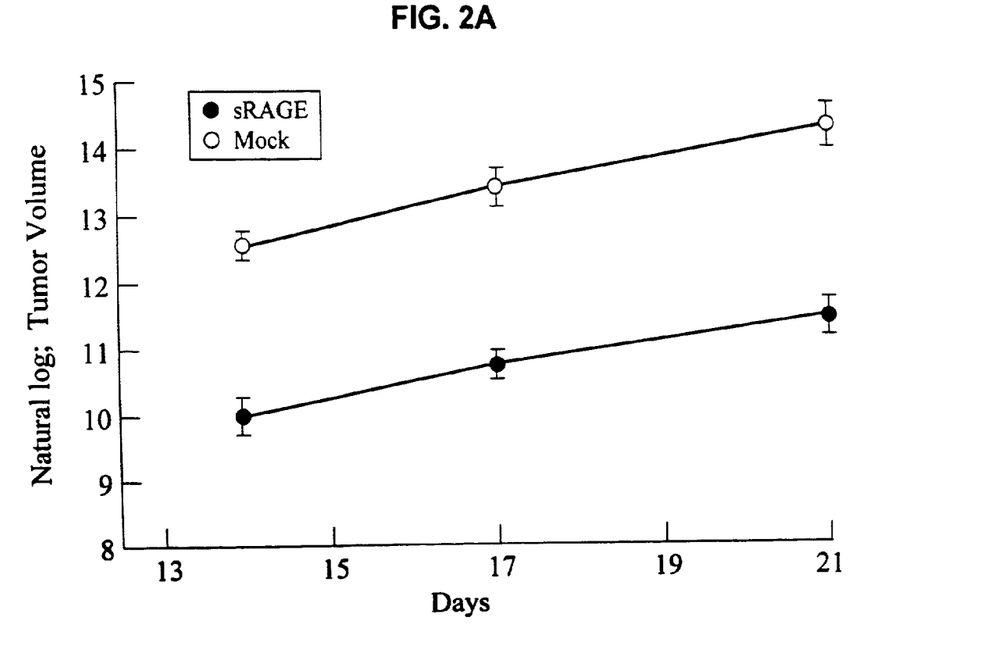
FIGS. 2A–2B. The growth rate of sRAGE-transfected tumor cells is not different than that of mock-transfected tumor cells, in vivo. The rate of tumor cell growth was calculated and the slope of the line determined (± standard error) using Microsoft Excel. The y axis represents the natural logarithm of the tumor volume and the x axis represents time (days). These studies indicated that the slope of the growth curve for mock-transfected tumor cells was 0.247±0.025. For sRAGE-transfected tumor cells, the slope of the growth curve was 0.241±0.029.
Figure 2B:
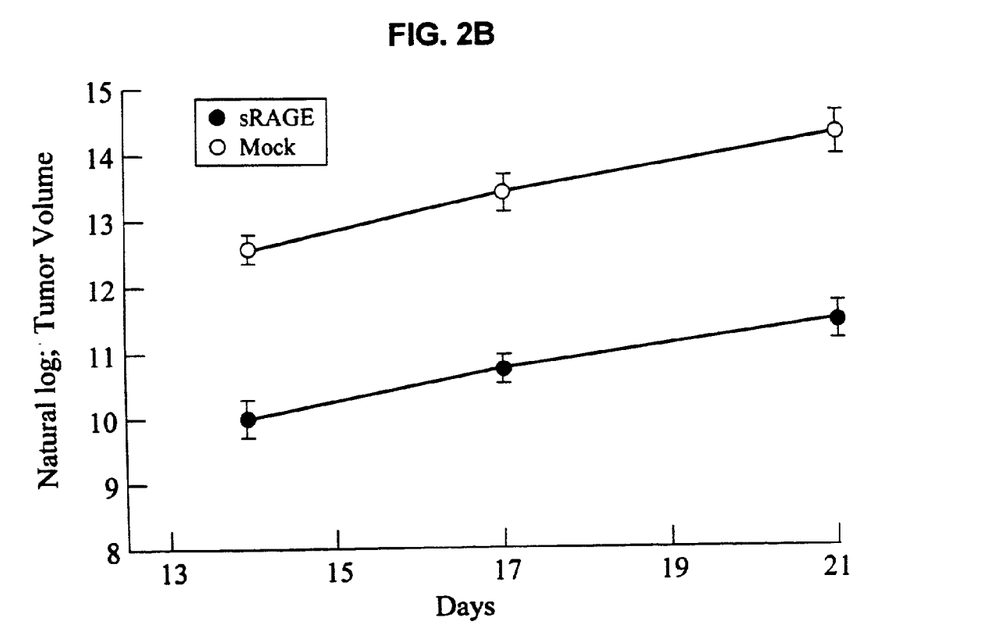

The growth rate of the transfected tumor cells (sRAGE and mock) derived from analysis of the above in vivo data revealed that there was no difference between the rate of growth of sRAGE-transfected C6 glioma cells compare with those mock-transfected (FIG. 2). When the natural log of tumor volume was plotted vs time, the slope of the growth curve for mock-transfected tumor cells the slope of the growth curve was $0.241 \pm 0.025$. These data are consistent with the concept that sRAGE does not alter cellular replication. Rather, they suggest that the interaction of tumor cells with their local environment is affected in a manner inconsistent with their local spread and invasion.

Figure 3A:
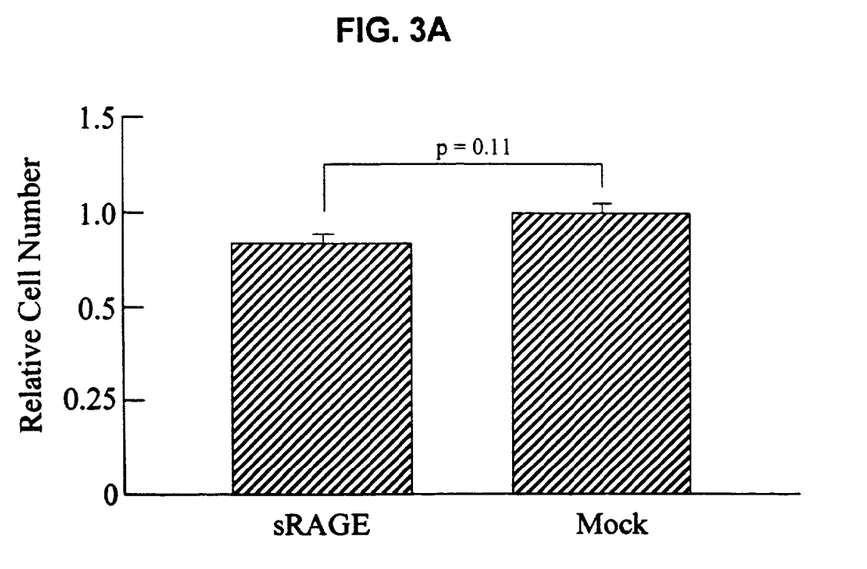
FIGS. 3A–3B. The rate of growth of sRAGE-transfected tumor cells is similar to that of mock-transfected tumor cells in in vitro studies. C6 glioma cells transfected with either sRAGE or mock were placed into 96 well tissue culture wells. On day three after onset of incubation, cells were fixed and stained and relative cell number assessed using the CYQUANT® assay from AMERSHAM®. These studies indicated that the relative cell number of sRAGE-transfected C6 cells on day three was 0.90±0.03 and 1.0±0.04 in mock-transfected C6 tumor cells (p=0.11).
Figure 3B:
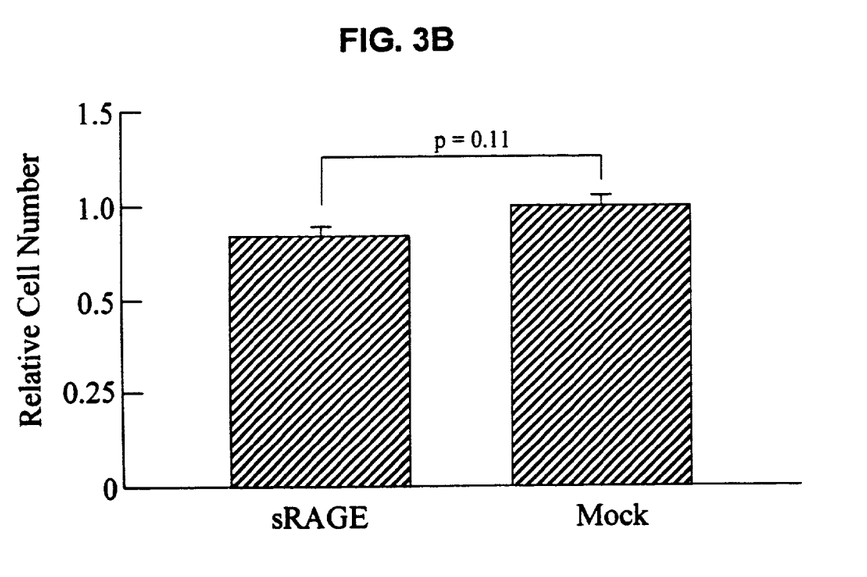

To further confirm that transfection of sRAGE into C6 glioma cells did not alter the rate of tumor growth, we demonstrated that when sRAGE-transfected or mock transfected C6 glioma cells were grown in culture, no difference in the cell number was observed at three days incubation (FIG. 3). Using a colormetric assay system from Amersham for quantitation of cell number, on day three, relative cell number of sRAGE-transfected C6 cells was $0.90 \pm 0.03$ vs. $1.0 \pm 0.04$ in mock-transfected C6 tumor cells ($p=0.11$). These data were further suggestive of the importance of sRAGE in limiting tumor cell growth and spread into the local tumor environment in vivo and suggest that sRAGE does not impact on cellular replication processes.

Systemic Administration of sRAGE

Figure 4A:
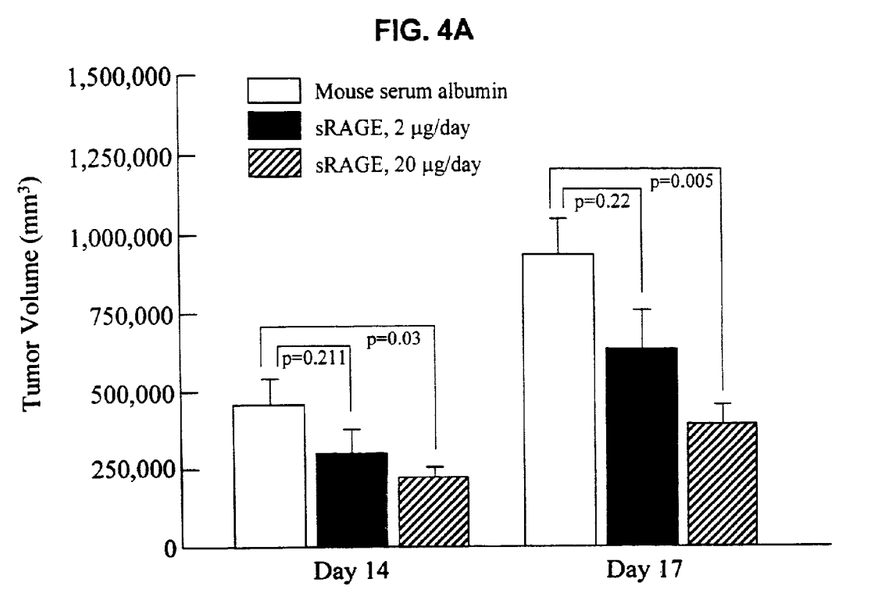
FIGS. 4A–4B. Systemic administration of sRAGE results in diminished tumor volume in C6 glioma cells injected into nude mice. C6 glioma cells ($1 \times 10^5$/ml; 0.1 ml) were injected into the backs of nude mice. Immediately after injection, once daily injections of either mouse sRAGE (20 or 2 µg/day) or mouse serum albumin (MSA; 40 µg/day) were begun intraperitoneally. Tumor volume was measured on days 14 and 17 after injection. For each experimental group, n-10. Statistical considerations are indicated.
Figure 4B:
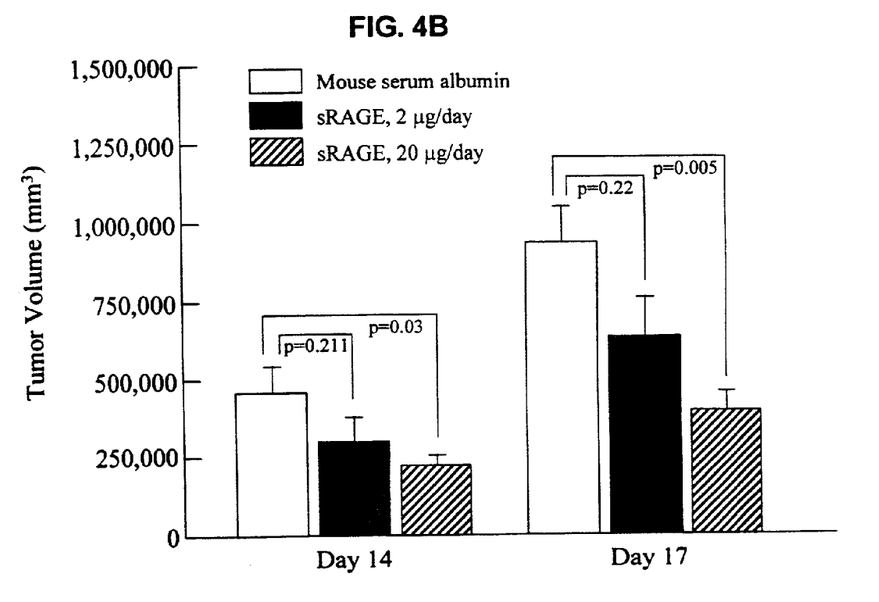

In order to further delineate the role of sRAGE in limiting tumor growth and invasion into the local environment, C6 tumors were established in NCR nude mice by injection of $10^5$ cells/ml (0.1 ml) C6 glioma cells (without transfection). Immediately after injection of tumor cells, intraperitoneal administration of sRAGE was begun (either 20 or 2 µg/day) or mouse serum albumin (FIG. 4). On day 14, mean tumor volume in MSA-treated mice was $459,000 \pm 87,457.6$ $\mu m^3$. In mice treated with sRAGE, 20 µg/day, however, mean tumor volume was decreased 2-fold ($225,000 \pm 38,054$ $\mu m^3$; $p=0.03$). In contrast, mice treated with sRAGE, 2 µg/day, demonstrated no significant change in tumor volume (305,000±79,998; $p=0.21$ [when compared with those treated with MSA]}. On day 17, mean tumor volume in MSA-treated mice was $935,000 \pm 117,499$ $\mu m^3$. In contrast, mice treated with sRAGE, 2 µg/day, demonstrated no significant change in tumor volume ($637,000 \pm 127,698$ $\mu m^3$; $p=0.22$ [when compared with those treated with MSA]).

Figure 5A:
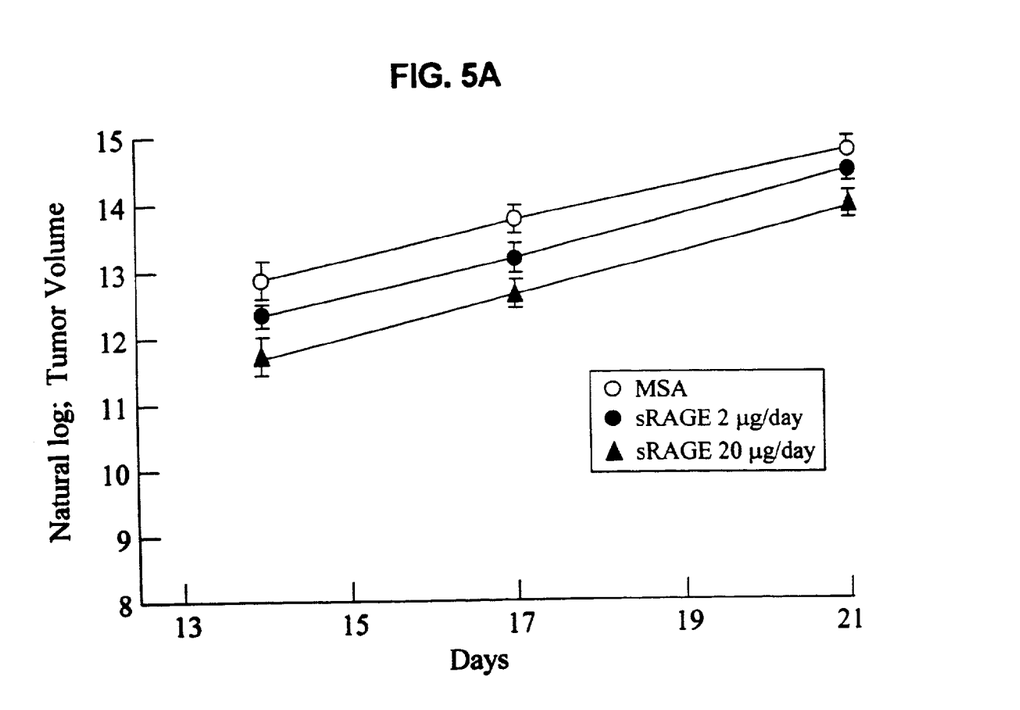
FIGS. 5A–5B. The rate of growth of C6 glioma cells is similar in sRAGE and MSA-treated mice in vivo. The rate of tumor cell growth was calculated and the slope of the line determined (± standard error) using Microsoft Excel. The y axis represents the natural logarithm of the tumor volume and the X axis represents time (days). The slope of the growth curve for C6 glioma tumor cells grown in the presence of mouse serum albumin was 0.264±0.03. The slopes of the growth curve for C6 glioma cells grown in the presence of sRAGE (20 vs. 2 µg/ml) were not different (0.311±0.04 and 0.313±0.04, respectively).
Figure 5B:
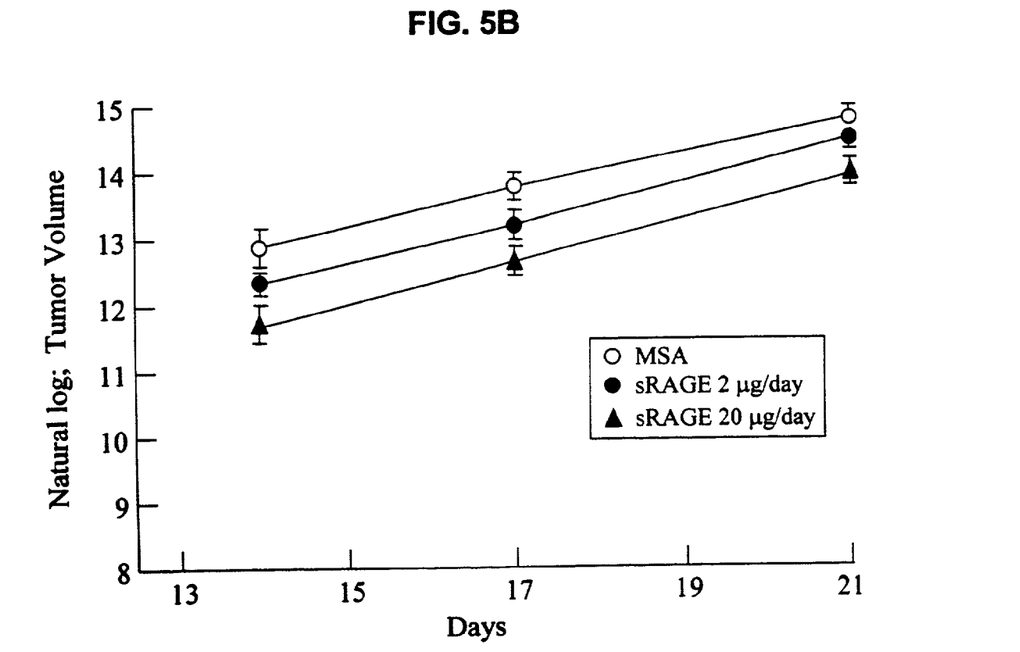

When the growth rate of the tumor cells was plotted, no apparent differences were noted among tumors in mice treated with sRAGE (both doses) or mouse serum albumin (FIG. 5). When the natural log of the tumor volume was plotted vs. time, the slope of the growth curve for C6 glioma tumor cells grown in the presence of mouse serum albumin was $0.264 \pm 0.03$. The slopes of the growth curve for C6 glioma cells grown in the presence of sRAGE (20 vs. 2 µg/ml) were not different ($0.311 \pm 0.04$ and $0.313 \pm 0.04$, respectively). These data further support the hypothesis that sRAGE does not impact on cellular replication; rather, sRAGE appears to inhibit cellular interaction with matrix components that is necessary for tumor impingement in the local environment.

Figure 6A:
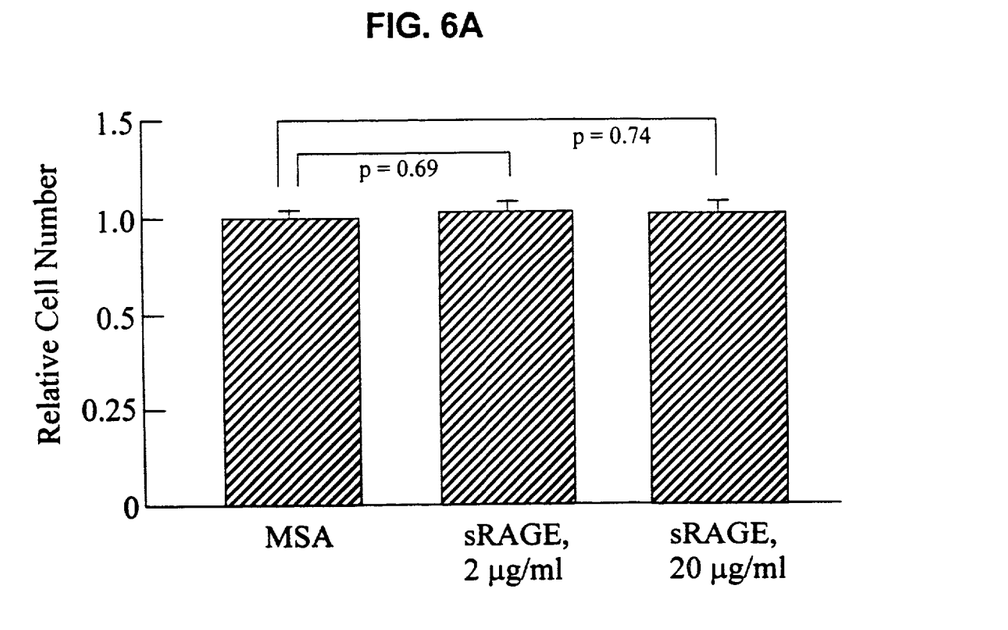
FIGS. 6A–6B. The rate of growth of tumor cells is similar in the presence of either sRAGE or mouse serum albumin in in vitro studies. C6 glioma cells were placed into 96 well tissue culture wells and grown in the presence of either sRAGE (20 or 2 µg/ml) or mouse serum albumin (40 µg/ml). On day three after onset of incubation, cells were fixed and stained and relative cell number assessed using the CYQUANT® assay from AMERSHAM®. Relative cell number (day three) of cells treated with MSA was 1.0±0.045. Similarly, relative cell number in the presence of sRAGE (20 or 2 µg/ml) was 1.03±0.06 and 1.02±0.06, respectively. Statistical considerations are shown.
Figure 6B:
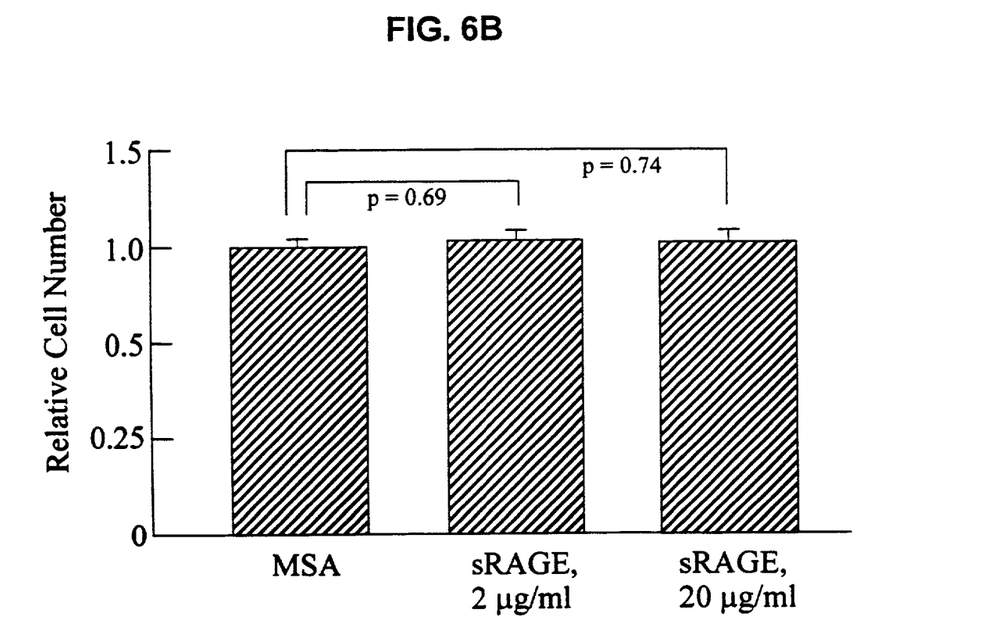

Finally, when C6 cells were cultured in the presence of sRAGE (high and low doses; 20 and 2 µg/ml) or mouse serum albumin, no apparent difference in relative cell number was observed (FIG. 6). Relative cell number (day three) of cells treated with MSA was $1.0 \pm 0.045$. Similarly, relative cell number in the presence of sRAGE (20 or 2 µg/ml) was $1.03 \pm 0.06$ and $1.02 \pm 0.06$, respectively. These data further support the concept that sRAGE does not impact upon cellular proliferation; rather, it more likely affects the ability of tumor cells in vivo to grow and extend into their local environment.

DISCUSSION

A number of factors have been suggested to be important in the ability of tumors to grow and invade their local environment. Central to these involves processes such as angiogenesis, the ability of the tumors to develop tumor-specific vasculature; matrix degradation, in which the ability of matrix metalloproteinases (MMPs) to degrade the surrounding matrix is critical for the local spread and invasiveness of tumors; inhibition of the action of tissue inhibitors of metalloproteinases (TIMPs), whose natural function is to inhibit the activity of MMPs; and integrin-cell/integrin/matrix interactions, reactions in which specific ligand-receptor contact initiates signaling cascades that eventuate in tumor spread (14–25).

Certainly, a multitude of factors have been postulated to result in local tumor growth and invasion. In the present studies, the ability of sRAGE to result in diminished tumor volume appears to result not from a direct effect of sRAGE on cellular replication processes. Rather, the interaction of tumor cells with their local environment appears hampered. We postulated that perhaps one means by which this occurs is by inhibition of the tumor RAGE-matrix amphoterin components. Amphoterin and likely related structures have been suggested to activate plasminogen, thereby effecting one means by which, for example, MMPs may be activated in the tumor environment. It is quite possible, however, that additional, as yet unidentified mechanisms exist by which sRAGE exerts beneficial effects in this model.

A current focus of this work is to study the effects of sRAGE in a model of tumor metastases and distal invasion. At this time, studies are underway utilizing Lewis lung carcinoma cells; a model in which distant invasion of the tumor into the pleura and lung parenchyma ensues after removal of the primary lesion (placed onto the lower back of the mice)

In conclusion, while precise mechanisms underlying the beneficial effects of sRAGE are under study in this model of local tumor growth, our data suggest that sRAGE may represent a novel structure in the design of agents to limit tumor spread and invasion. In this context, sRAGE may also exert beneficial effects in the prevention of tumor distal growth and metastases.

REFERENCES

1. Schmidt, A-M., et al. J. Biol. Chem. 276: 14987–14997, 1992.
2. Neeper, M., et al. J. Biol. Chem. 267: 14998–15004, 1992.
3. Hori, O., et al. J. Biol. Chem. 170: 25752–25761, 1995.
4. Yan, S. D., et al. Nature 382: 685–691, 1996.
5. Yan, S. D., et al. Proc. Natl. Acad. Sci. 94: 5296–5301, 1997.
6. Schmidt, A-M., et al. In *Hormones and Signalling*, Volume I, Academic Press, p. 41–63, 1997.
7. Rauvala, H. and Pihlaskari, R. J. Biol. Chem. 262: 16625–16635, 1987.
8. Merenmies, J., et al. J. Biol. Chem. 266: 16722–16729, 1991.
9. Salmivirta, M., et al. Exp. Cell Res. 200: 444–451, 1992.
10. Mohan, P S, J., et al. Bioc. And Biophyx. Res. Comm. 182: 689–696, 1992.
11. Parkkinen, J., J. Biol. Chem. 268: 19726–19738, 1993.
12. Parkkinen, J. and H. Rauvala. J. Biol. Chem. 266: 16730–16735, 1991.
13. Singh, S. P., et al. Neuroreport 8: 2359–2363, 1997.
14. Price, J. T., et al. Critical Reviews in Biochemistry and Molecular Biology. 32: 175–253, 1997.
15. Timar, J., et al. Anticancer Research 16(6A): 3299–3306, 1997.
16. DeVries, T J, et al. Pathology, Research and Practice 192: 718–733, 1996.
17. Kubota, S., et al. International J. Cancer 70: 106–111, 1997.
18. Powell, W C and L M Matrisian. Current Topics in Microbiology and Immunology 213:1–21, 1996.
19. Seiki, M. Current Topics in Microbiology and Immunology 213: 23–32, 1996.
20. Byers S W, C L Sommers, B. Hoxter, A M Mercurio and A J Tozeren. Cell Science 108: 2053–2064, 1995.
21. Yoneda, J., et al. Experimental Cell Research 217: 169–179, 1995.
22. Tsang, T C, et al. Cancer Research 54: 882–886, 1994.
23. Grant D S, et al. Pathology, Research and Practice. 190: 854–863, 1994.
24. Spiegel, S., et al. Breast Cancer Research and Treatment 312: 337–348, 1994.
25. Thorgeirsson, U P, et al. J. Neuro-Oncology 18: 89–103, 1993.

What is claimed is:

1. A method for evaluating the ability of an agent to inhibit tumor cell spreading which comprises:
    (a) admixing with cell culture media an effective amount of an agent known to inhibit the interaction between RAGE (SEQ. ID. NO:1) on a tumor cell and a matrix coated with an extracellular matrix molecule selected from the group consisting of a cadherin, an integrin and a hyaluronic acid, wherein the agent is selected from the group consisting of a peptide, a peptidomimetic, a synthetic organic molecule, an inorganic molecule, a carbohydrate, a lipid, and a fragment of an antibody;
    (b) contacting the tumor cell in cell culture with media from step (a);
    (c) determining the amount of spreading of the tumor cell in the cell culture; and
    (d) comparing the amount of spreading of the tumor cell determined in step (c) with the amount determined in the absence of the agent, thus evaluating the ability of the agent to inhibit tumor cell spreading.

2. The method of claim 1, wherein the tumor cell is a cell from a subject.

3. The method of claim 2, wherein the subject is a human, a mouse, a rat, a dog or a non-human primate.

4. The method of claim 1, wherein the integrin is an αVβV integrin, an αVβIII integrin, or an αIβII integrin.

5. The method of claim 1, wherein the extracellular matrix molecule is a cadherin.

6. The method of claim 1, wherein the extracellular matrix molecule is an integrin.

7. The method of claim 1, wherein the extracellular matrix molecule is a hyaluronic acid.

* * * * *